(12) United States Patent
Rose et al.

(10) Patent No.: US 7,192,716 B2
(45) Date of Patent: Mar. 20, 2007

(54) ORGAN TRANSPLANT REJECTION AND ASSOCIATED CONDITIONS

(76) Inventors: Marlene Lydia Rose, 2 Princes Gardens, London (GB) W515D; Michael John Dunn, 2 Princes Gardens, London (GB) W515D (*) Notice: Subject to any disclaimer, the term of this patent is extended or adjusted under 35 U.S.C. 154(b) by 124 days.

(21) Appl. No.: 10/343,132

(22) PCT Filed: Jul. 30, 2001

(86) PCT No.: PCT/GB01/03393

§ 371 (c)(1),
(2), (4) Date: May 9, 2003

(87) PCT Pub. No.: WO02/10755

PCT Pub. Date: Feb. 7, 2002

(65) Prior Publication Data

US 2003/0175811 A1    Sep. 18, 2003

(30) Foreign Application Priority Data

Jul. 28, 2000    (GB)    .................. 0018614.8

(51) Int. Cl.
*G01N 33/53*    (2006.01)
(52) U.S. Cl. ............... 435/7.1; 436/501; 436/518; 436/811; 435/7.92
(58) Field of Classification Search ............ 435/7.1, 435/7.92–7.94, 973, 975; 436/501, 518, 436/524, 164, 172, 808, 811
See application file for complete search history.

(56) References Cited

U.S. PATENT DOCUMENTS

| | | | |
|---|---|---|---|
| 5,534,431 A | | 7/1996 | McDonald |
| 5,710,008 A | * | 1/1998 | Jackowski ............ 435/7.4 |
| 5,716,787 A | * | 2/1998 | Dunn et al. ........... 435/7.1 |
| 5,840,477 A | | 11/1998 | Seidman |
| 5,939,270 A | * | 8/1999 | Hauns.o slashed. et al. . 435/7.1 |
| 6,197,599 B1 | * | 3/2001 | Chin et al. ............ 436/518 |

FOREIGN PATENT DOCUMENTS

| | | |
|---|---|---|
| EP | 0330080 A2 | 2/1989 |
| EP | 0357856 A1 | 3/1990 |
| GB | 2268935 A | 1/1994 |
| WO | WO 93/03381 A1 | 2/1993 |
| WO | WO 00/20448 A2 | 4/2000 |
| WO | WO 01/40302 A2 | 6/2001 |

OTHER PUBLICATIONS

Volk et al., Serum levels of soluble interleukin-2 receptor, C-reactive protein, neopterin, myoglobin and light chains of cardiac myosin fail to correlate with the occurrence of rejection, Clinical Transplantation 1992: 6: 21-26.*
Gash et al., Serum myoglobin does not predict cardiac allograft rejection, Jour heart Lung Transplant, May-Jun. 1994; 13(3); 451-454.*
Vivekananthan et al., Are biochemical indices of acute cardiac inkury useful in predicting cardiac allograft rejection, Transplantation 1998; 65 (12): S-156.*
Suzow et al., Increased expression of heat shock proteins during acute cardiac allograft rejection, Human Immunology, vol. 44, 1995, pp. 120, 6.6 #155.*
Kelly et al., Prediction of acute cellular rejection by serum troponin I, myoglobin, ck-mb mass and ck-mb in outpatient orthopic heart transplant recipients, Journal of Investigative Medicine, Jan. 1998, vol. 46, No. 1, pp. 64A.*
Yamasa Products, Diagnostics, YSI-7709, Mosin LI Kit Yamasa, www.yamasa,com/shindan/english/seihin.htm.*
Kawauchi, Motohiro, et al., "Diagnosis of Cardiac Allograft Rejection by the Detection of Circulating PLasma Cardiac Myosin Light Chains"; Japanese Journal of Surgery, 20: 212-216 (1990).
Kovalyov, Leonid I., et al., "The major protein expression profile and two-dimensional protein database of human heart"; Electrophoresis, 16:1160-1169 (1995) and Database Swiss-PROT 'Online! Accession No. P10916, MLC-2, Feb. 4, 2002 XP002189188 abstract.
Watkins, Hugh, et al., "Mutations in the Genes for Cardiac Troponin T and Alpha-Tropomyosinin Hyertrophic Cardiomyopathy"; New England Journal of Medicine, 332: 1058-1064 (1995).
Hwang, David M., et al., "Identification of Differentially Expressed Genes in Cardiac Hypertrophy by Analysis of Expressed Sequence Tags"; Genomics, 66: 1-14 (2000).
U.S. Appl. No. 10/148,341, filed Nov. 12, 2002, Marlene Lydia Rose et al.

* cited by examiner

Primary Examiner—Long V. Le
Assistant Examiner—Gary W. Counts
(74) Attorney, Agent, or Firm—Dann, Dorfman, Herrell and Skillman, P.C.; Patrick J. Hagan, Esq.

(57) ABSTRACT

Protein markers associated with organ transplant rejection and associated conditions are disclosed, and in particular materials and methods relating to the diagnosis and treatment of acute rejection. Examples of markers include a-Crystallin b-chain Tropomyosin a-chain and Myosin Light Chain 1.

11 Claims, 3 Drawing Sheets

Fig. 3
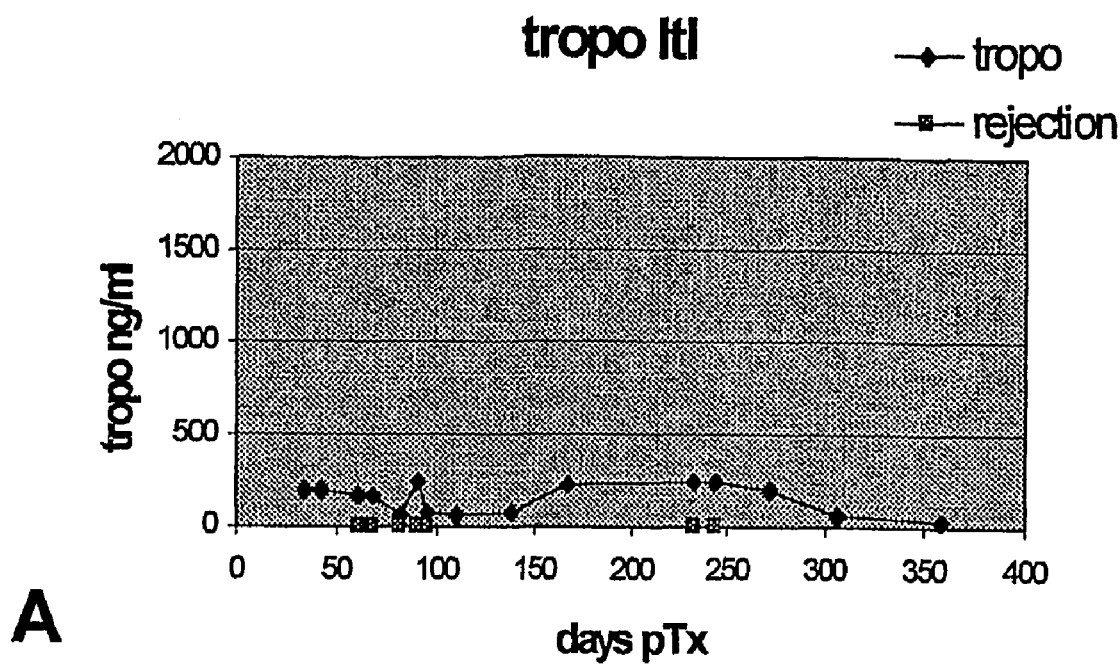
A
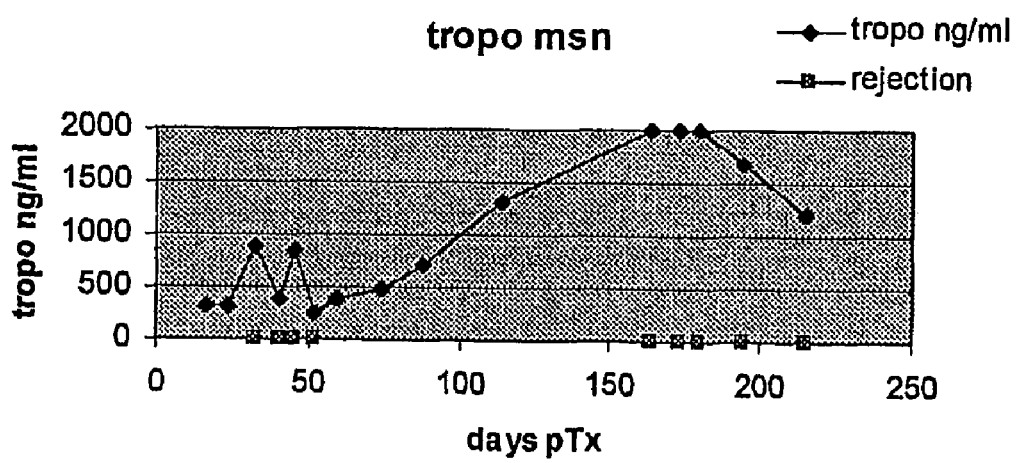
B

ORGAN TRANSPLANT REJECTION AND ASSOCIATED CONDITIONS

FIELD OF THE INVENTION

The present invention relates to organ transplant rejection and associated conditions, and in particular to materials and methods for the diagnosis, prognosis or treatment of acute rejection following solid organ transplantation.

BACKGROUND OF THE INVENTION

Approximately 55,000 solid organ transplants are performed worldwide every year. This comprises approximately 10,000 hearts, 35,000 kidneys, 16,000 livers, and 2,000 lungs. Rejection remains the most common complication following transplantation and is the major source of morbidity and mortality. There are generally recognised to be three types of organ rejection; hyperacute, acute and chronic. Hyperacute rejection occurs within 24 hours of the transplant and is readily apparent. Acute rejection is generally regarded as rejection that occurs within the first six months of transplantation, is mediated by mononuclear cells infiltrating the graft causing acute damage to graft parenchymal cells. It is usually reversed by anti-T cell cytolytic therapy. Chronic rejection, generally regarded as that occurring at least six months after transplantation, is very difficult to diagnose clinically and usually presents as a gradual vasculopathy (i.e. occlusion) of grafted vessels.

Constant vigilance is required to monitor the immune response to the grafted organ in the first 3 months, when acute rejection is most likely to occur. After kidney transplantation, raised levels of serum creatinine and urea are an indication of failing graft function, but do not specifically denote immunological damage to the graft. Nevertheless these are commonly used to detect kidney rejection, with renal biopsies used only occasionally. In contrast, monitoring the function of transplanted hearts and lungs relies entirely on histological or clinical parameters. There are no existing methods of non-invasively detecting heart or lung transplant rejection.

Thus, for patients undergoing cardiac transplantation, surveillance endomyocardial biopsies are taken at weekly intervals to 6 weeks, then at 2 weekly intervals until 3 months. In addition, any positive biopsy is followed-up by a repeat biopsy one week later to ensure that anti-rejection therapy has been successful. Patients also undergo further biopsies when clinically indicated. For example, every heart transplant patient has a minimum of 9 biopsy procedures in the first year. Lung function is routinely measured by the patients themselves using a spirometer on a daily basis. Any unexplained persistent fall in lung function will be followed up by transbronchial biopsy to confirm the diagnosis by histology. It is especially important to obtain a differential diagnosis between rejection and infection after lung transplantation. For this reason the transbronchial biopsy procedure is usually accompanied by bronchiolar lavage, which is sent for culture and bacteriological analysis.

Routine histological analysis of cardiac biopsies remain the cornerstone of management after heart transplantation and any new methods of detecting rejection are compared to the histological grading of biopsies, which are still regarded as the gold standard. A standardised nomenclature and grading system of both hearts and lungs was suggested in 1990 (1,2) and is now used by the majority of centres. However, the endomyocardial biopsy procedure is unpleasant for the patient, is associated with a small chance of complications, and is highly labour intensive and expensive. It would be of huge benefit to the patient and the hospital to have a non-invasive method to replace the endomyocardial biopsy. In theory, there are many possibilities of non-invasively detecting rejection including non-invasive monitoring of heart function such as magnetic resonance imaging (3), signal averaged electrocardiogram (4), specialised echocardiographic indices (5) and looking for markers in peripheral blood. There are two major approaches in employing blood markers; one is to exploit what is known about activation of the recipient's immune system and the second is to look for markers of graft damage.

Over the last 10 years, there has been an explosion of knowledge regarding the effect of the allograft on the immune system. Rejection is initiated by CD4+ recipient T lymphocytes recognising foreign MHC Class II molecules on antigen presenting cells in the donor graft. This initiates a cascade of cytokines that may be acting directly to damage graft parenchymal cells or maybe acting to recruit and amplify further effector mechanisms such as CD8+ T cells, macrophages and B cells. In heart transplantation, where there can be dissociation between the size of the infiltrate and the extent of cardiac haemodynamic compromise, it is thought TNF-α and nitric oxide may have negative inotropic effects on beating myocytes Over the years there have been numerous attempts to find signs of immune activation in peripheral blood. These have included examining peripheral blood for levels of IL-2, soluble IL-2R, IL-6, IL-7, IL-8, TNF-α, IFN-γ, soluble ICAM-1, soluble MHC antigens, activated T cells and T cell populations and cytoimmunological monitoring (6). Often these are cross sectional studies and when results are pooled (i.e. comparison made between rejection and non-rejection) significant differences can be obtained. However, when one performs longitudinal studies of individual patients, the values for a particular maker vary so widely on a daily or weekly basis that sensitivities and specificities so derived are inadequate for practical use. It is clear that the immune system is highly labile for the first 3 months, when most rejection episodes occur. It will certainly be modified by augmented immunosuppression both directly (e.g. anti-thymocyte globulin binds to soluble HLA and adhesion molecules) and indirectly, by altering the balance of cell subpopulations as they recover from depletion. Taken as whole, these immune activation markers are always elevated compared to non-transplant patients, but are not reliable indicators of rejection within the individual transplant patient.

One possible reasons for the low specificity and sensitivity of the prior art markers is that they do not distinguish between rejection and infection. In order to circumvent this problem, investigations have been made to try and distinguish between donor specific and third party T cell responses as a way of assessing the state of the patient's immune system (7, 8).

We have also addressed the issue of where one would expect to find donor-specific lymphocytes, in the peripheral circulation or in the graft. To this end, we cultured lymphocytes from patients' endomyocardial biopsies and performed a limiting dilution analysis to quantify numbers of cytotoxic precursor cells with donor specific or third party specificity. At the same time, lymphocytes were cultured from patients' blood and we made a comparison of the precursor frequencies of donor specific cells found in blood and the graft. The results showed the presence of donor-reactive CD8+ T cells during rejection, but they were found almost exclusively in the graft, not in the blood. This diminishes the chances of finding specific reactivity in the peripheral circulation unless a particular sensitive assay is used. The same argument can be used for detection of circulating cytokines. It has been shown that high levels of IL-6 and soluble TNF-R1 (TNF receptor) in coronary sinus, but not aortic blood, correlated with poor coronary vasomotor tone during rejection episodes (9).

Interestingly donor specific alloantibody is produced during cell mediated acute rejection episodes in some patients (10) but this is unlikely to be a rapid enough response with which to monitor patients. An association between blood eosinophil counts and acute cardiac and pulmonary allograft rejection has been recently reported (11) whether this is specific and sensitive enough to be of practical use remains to be seen.

In the early days of heart transplantation (circa 1970's), before advent of cyclosporine, conventional serological markers of cardiac damage (lactate dehydrogenase, creatine kinase) were used as markers of graft failure. However, they lacked sensitivity and were often found to be elevated too late to reverse rejection of cardiac allografts. Troponin is a contractile regulatory complex found in striated and cardiac muscle. It consists of 3 distinct polypeptide components; troponin C, (the calcium binding element), troponin I (the actinomyosin ATPase inhibitory element) and troponin T (the tropomyosin binding element). The complex serves to regulate the calcium dependent interaction of myosin and actin and thus plays an integral role in muscle contraction.

In the 1990s, specific enzyme immunoassays have been developed against cardiac specific isoforms of troponin T and troponin I, which show little cross reactivity with the isoforms from skeletal muscle (12). With the currently commercially available kits, circulating troponin T or troponin I is only detectable in the circulation of patients with severe cardiac muscle damage such as myocardial infarction (13) or after cardiac surgery (14). Katus first reported that use of troponin T to monitor heart rejection was limited by the observation that high levels were found in the first few days after transplantation, and levels remained well above normal for 2–3 months (15). This was not related to ischaemic time and the reasons for these elevated levels are still unclear. They probably reflect low-level immunological damage caused by humoral factors (antibodies or cytokines). For this reason, the assay cannot be used to monitor rejection in the first three months, when rejection is most likely to occur. After this period, the assay does detect grade 3 or 4 rejection with a high sensitivity of 80.4% and a strong negative predictive value of 96.2% (16). It has also been used in patients six months after transplantation where rising levels are said to predict chronic rejection (17). An interesting adaptation of this assay to transplantation has been to measure levels of serum troponin T in donors; high levels correlated with occurrence of rejection in the recipients of such hearts (18), presumably reflecting damage and release of graft antigens to be recognised by the immune system.

From the above discussion, it will be apparent that it remains a continuing problem in the art to find markers which can provide an accurate and early diagnosis of acute rejection.

SUMMARY OF THE INVENTION

Broadly, the present invention relates to markers associated with organ transplant rejection and associated conditions, and in particular provides materials and methods for the diagnosis, prognosis or treatment of acute rejection and in particular acute rejection following solid organ transplantation.

The approaches in looking for markers in the prior art has required a prior knowledge of the processes involved in acute rejection and then utilised this knowledge to select prospective markers. The present invention adopted an alternative, global approach that requires no prior knowledge or assumptions, namely to look for any changes in tissue or serum associated with acute rejection with the aim of identifying diagnostic and/or prognostic markers of acute rejection following solid organ transplantation. The approach being used is to identify by 2-DE analysis of sequential endomyocardial biopsy tissue samples, changes in protein expression that either proceed or occur during periods of acute rejection. These potential markers of acute rejection are then identified and characterised using microchemical methods such as mass spectroscopy. Mono- and/or polyclonal antibodies specific for these proteins are then used in sensitive immunoassays to establish whether these proteins can be detected in the plasma of transplant patients. Proteins identified in this way are then potential candidates for use as a non-invasive diagnostic and/or prognostic test for acute rejection. The proteins can then be evaluated as markers by screening of large numbers of serum samples from transplant patients with and without acute rejection using the immunoassays for detecting these marker or antibodies raised in response to them.

Accordingly, in a first aspect, the present invention provided the use of the presence or amount of a protein set out in Table 2, or a fragment thereof, as a marker for the diagnosis and/or prognosis of acute rejection and associated conditions.

In a further aspect, the present invention provides a method of diagnosing acute rejection or associated conditions, e.g. following solid organ transplantation, the method comprising determining the presence or amount of a protein set out in Table 2, or a fragment thereof, or antibodies against these proteins, in a sample from a patient.

In a preferred embodiment, the method comprises the steps of:
(a) contacting a sample from a patient with a solid support having immobilised thereon a binding agent having binding sites which are capable of specifically binding to the antibody or antigen under conditions in which the antibody or antigen bind to the binding agent; and,
(b) determining the presence or amount of the antibody or antigen bound to the binding agent.

In one embodiment, step (b) comprises (i) contacting the solid support with a developing agent which is capable of binding to occupied binding sites, unoccupied binding sites or the antibody or antigen, the developing agent comprising a label and (ii) detecting the label to obtain a value representative of the presence or amount of the antibody or antigen in the sample. Examples of labels are set out below. In one convenient embodiment, the label is an enzyme which produce a detectable result by acting on a substrate, e.g. in ELISA type assay. In alternative embodiment, the analyte is detected in step (b) by tagging, to allow it to be detected when it binds to the binding agent in the array. Tagging techniques are well known in the art.

In some embodiments, the method uses immobilised protein in an assay for antibodies (e.g. anti-endothelial antibodies) in a sample which are capable of binding to the protein. Alternatively, the protein may be the target analyte of the assay, e.g. binding to immobilised antibodies on the solid support. Preferred formats of assays are described in more detail below.

In order to provide a method of diagnosis and/or prognosis which is more precise than the prior art, the method can optionally be used to determine the presence or amount of a plurality of protein markers or antibodies associated with organ transplant rejection in a sample from a patient. Conveniently, the assays for the different markers can be carried out employing a plurality of different binding agents, each binding agent being specific for a different analyte in the sample, the binding agents being immobilised at predefined (i.e. spatially separated) locations on the solid support.

In a further aspect, the present invention provides a kit for use in the diagnosis or prognosis of acute rejection by determining the presence or amount of an analyte selected from the markers set out in Table 2, or a fragment thereof, or antibodies against these antigens, in a sample from a patient, the kit comprising:
  (a) a solid support having a binding agent capable of binding to the analyte immobilised thereon;
  (b) a developing agent which is capable of binding to occupied binding sites, unoccupied binding sites or the antibody or antigen, the developing agent comprising a label;
  (c) one or more components selected from the group consisting of washing solutions, diluents and buffers.

In a further aspect, the present invention provides the use of a protein set out in Table 2 or a fragment thereof, or antibodies capable of specifically binding these proteins for the preparation of a medicament for the treatment of acute rejection and associated conditions.

Embodiments of the invention will now be described in more detail by way of example and not limitation with reference to the accompanying figure.

BRIEF DESCRIPTION OF THE FIGURES

FIGS. 3A and B show the results of ELISA assays using tropomvosin as a marker of acute rejection.

DETAILED DESCRIPTION

Organ Transplant Rejection

Figure 1:
FIG. 1 shows a 2D gel identifying protein markers for the diagnosis of acute rejection.

The present invention concerns the diagnosis, prognosis and treatment of acute rejection of transplanted organs and associated conditions. As used in the art, acute rejection is the form of rejection that occurs within the first six months of transplantation, is mediated by mononuclear cells infiltrating the graft causing acute damage to graft parenchymal cells. It is usually reversed by anti-T cell cytolytic therapy.

The protein and antibody markers described herein can be used in the diagnosis, prognosis or treatment of rejection of transplanted organs, including solid transplanted organs such as heart, kidney, liver or lung, and other transplanted tissue such as pancreas and small bowel, and pathological conditions associated with acute organ or tissue rejection.

Assays

Methods for determining the concentration of analytes in samples from individuals are well known in the art and readily adapted by the skilled person in the context of the present invention to determine the presence or amount of the protein markers or fragments thereof, or antibodies against the markers in a sample from a patient. The results of such assays can in turn allow a physician to determine whether a patient suffers from a condition or is at risk of developing acute rejection or an associated condition. It may also allow the physician to optimise the treatment of the conditions. Thus, this allows for planning of appropriate therapeutic and/or prophylactic treatment, permitting stream-lining of treatment by targeting those most likely to benefit.

The methods described herein are useful for both the diagnosis and/or prognosis of acute rejection. Acute rejection may be indicated if one or more markers is present at increased or decreased concentration. For some markers, both an increased or a decreased concentration may be indicative of acute rejection.

The methods typically employ a biological sample from patient such as blood, serum, tissue, serum, urine or other suitable body fluids. A preferred patient sample is blood.

The assay methods for determining the concentration of the protein markers or antibodies typically employ binding agents having binding sites capable of specifically binding to protein markers, or fragments thereof, or antibodies in preference to other molecules. Examples of binding agents include antibodies, receptors and other molecules capable of specifically binding the analyte of interest. Conveniently, the binding agents are immobilised on solid support, e.g. at defined, spatially separated locations, to make them easy to manipulate during the assay.

The sample is generally contacted with the binding agent(s) under appropriate conditions which allow the analyte in the sample to bind to the binding agent(s). The fractional occupancy of the binding sites of the binding agent(s) can then be determined either by directly or indirectly labelling the analyte or by using a developing agent or agents to arrive at an indication of the presence or amount of the analyte in the sample. Typically, the developing agents are directly or indirectly labelled (e.g. with radioactive, fluorescent or enzyme labels, such as horseradish peroxidase) so that they can be detected using techniques well known in the art. Directly labelled developing agents have a label associated with or coupled to the agent. Indirectly labelled developing agents may be capable of binding to a labelled species (e.g. a labelled antibody capable of binding to the developing agent) or may act on a further species to produce a detectable result. Thus, radioactive labels can be detected using a scintillation counter or other radiation counting device, fluorescent labels using a laser and confocal microscope, and enzyme labels by the action of an enzyme label on a substrate, typically to produce a colour change. In further embodiments, the developing agent or analyte is tagged to allow its detection, e.g. linked to a nucleotide sequence which can be amplified in a PCR reaction to detect the analyte. Other labels are known to those skilled in the art are discussed below. The developing agent(s) can be used in a competitive method in which the developing agent competes with the analyte for occupied binding sites of the binding agent, or non-competitive method, in which the labelled developing agent binds analyte bound by the binding agent or to occupied binding sites. Both methods provide an indication of the number of the binding sites occupied by the analyte, and hence the concentration of the analyte in the sample, e.g. by comparison with standards obtained using samples containing known concentrations of the analyte.

In alternative embodiments, the analyte can be tagged before applying it to the support comprising the binding agent.

In a preferred format, the presence or amount of a marker set out in Table 2, or antibodies against these antigens, is determined in an ELISA assay.

There is also an increasing tendency in the diagnostic field towards miniaturisation of such assays, e.g. making use of binding agents (such as antibodies or nucleic acid sequences) immobilised in small, discrete locations (microspots) and/or as arrays on solid supports or on diagnostic chips. These approaches can be particularly valuable as they can provide great sensitivity (particularly through the use of fluorescent labelled reagents), require only very small amounts of biological sample from individuals being tested and allow a variety of separate assays can be carried out simultaneously. This latter advantage can be useful as it provides an assay employing a plurality of analytes to be carried out using a single sample. Examples of techniques enabling this miniaturised technology are provided in WO84/01031, WO88/01058, WO89/01157, WO93/08472, WO95/18376, WO95/18377, WO95/24649 and EP 0 373 203 A. Thus, in a further aspect, the present invention provides a kit comprising a support or diagnostic chip having immobilised thereon a plurality of binding agents capable of specifically binding different protein markers or antibodies, optionally in combination with other reagents (such as labelled developing reagents) needed to carrying out an assay. In this connection, the support may include binding agents specific for analytes such as vimentin, e.g. as disclosed in U.S. Pat. No. 5,716,787.

Expression of Proteins

Following the identification of the protein markers associated with acute rejection, large amounts of the protein may be produced using expression techniques well known in the art. The protein produced in this way may be used as a binding agent, immobilising it on solid support in an assay for antibodies in a sample from a patient, or as an immuogen to produce antibodies. Alternatively, the protein, or fragments thereof, may be used in the therapeutic treatment of organ transplant rejection, i.e. to ameliorate the deleterious effect of the antibodies.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

After transforming the host cells with the nucleic acid encoding the proteins, they an be produced by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers.

Antibodies

In alternative embodiments of the invention, antibodies capable of binding the protein associated with acute rejection may be needed, e.g. for use in assays to determine the presence or amount of a given protein in a sample or for therapeutic use in reducing the deleterious effect of a protein in vivo. Thus, the present invention also provides the production of antibodies having the property of specifically binding to the marker proteins identified herein, or fragments or active portions thereof.

The production of monoclonal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2 188 638 A or EP 0 239 400 A. A hybridoma producing a monoclonal antibody may be subject to genetic mutation or other changes, which may or may not alter the binding specificity of antibodies produced.

These antibodies may be specific in the sense of being able to distinguish between the polypeptide it is able to bind and other human polypeptides for which it has no or substantially no binding affinity (e.g. a binding affinity more than $10^3$, more preferably $10^4$ and more preferably $10^5$ times better than to unrelated molecules). Specific antibodies bind an epitope on the molecule which is either not present or is not accessible on other molecules. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357: 80–82, 1992). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

Antibodies for use in the assays described herein as binding or developing agents may be labelled. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine. Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Other techniques that can be sued to label antibodies include tagging, e.g. with a nucleotide sequence which can be amplified by PCR.

The mode of determining binding is not a feature of the present invention and those skilled in the art are able to choose a suitable mode according to their preference and general knowledge.

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid therefor. Antibodies may modulate the activity of the polypeptide to which they bind and so, if that polypeptide has a deleterious effect in an individual, may be useful in a therapeutic context (which may include prophylaxis).

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

Experimental

The following studies of acute rejection following heart transplantation were used to identify potential marker for the diagnosis and/or prognosis of acute rejection.

Patients and Endomyocardial Biopsy Samples

These studies were performed with Ethical Committee approval on patients undergoing heart transplantation at Harefield hospital. Sequential endomyocardial biopsies were collected from a cohort of 20 patients for the first 4 months following transplantation, with usually eight biopsy samples being collected over this time period. Serum samples were also been collected and stored for future evaluation of the acute rejection markers by immunoassay. One sample of each tissue biopsy was immediately frozen in liquid nitrogen, while a second sample was incubated for 20 hours in the presence of [$^{35}$S]-methionine to radiolabel those proteins that were newly synthesised. The radiolabelled proteins were separated immediately by 2-DE using both IPG 3–10 NL (to separate most, including basic proteins) and IPG 4–7 (to separate acidic to neutral proteins) pH gradients for the first IEF dimension. The frozen biopsies have been stored for possible future studies of acute rejection markers. Quantitative changes in protein synthesis using the [$^{35}$S]-met radiolabelled gels have been analysed using the PDQuest (Bio-Rad) software system.

Computer Analysis of 2-DE Profiles of Radiolabelled Proteins from Heart Biopsies Computer analysis of the 2-DE profiles of [$^{35}$S]-met radiolabelled proteins for patients with a complete 4-month set of biopsy samples, using IPG 3–10 NL pH gradients for the first IEF dimension was then carried out, and Table 1 summarises the result of this analysis for four of the patients in the study.

2-DE separations were also done for all of the samples using IPG 4–7 L pH gradients for the first, IEF dimension. This gave improved separation of the acidic to neutral proteins compared with the IPG 3–10 NL pH gradients (which give a broad overview of the sample proteins and also allow analysis of the basic proteins) described above. Computer analysis of this series of 2-DE protein profiles was used to find additional potential markers of rejection.

Chemical Characterisation of Potential Markers of Rejection

As described above, computer analysis has highlighted cardiac proteins that are potential markers of acute rejection. The best candidates for diagnostic/prognostic non-invasive markers (i.e. detectable in blood) are those proteins that are increased in association with rejection. Priority is being given to the chemical characterisation of these proteins, so that we can begin the process of establishing ELISA assays to determine whether these proteins can be detected in the serum of patients undergoing acute rejection. To date some 50 protein spots from the 2-DE gels have been submitted for protein characterisation using a combination of peptide mass fingerprinting by MALDI-MS and protein sequencing by ESI-MS/MS to characterise the proteins. So far we have definitive identifications for 13 proteins (FIG. 1, Table 2).

Detection of Anti-Heart Antibody Reactive Proteins

A complementary approach was then used to detect and identify potential markers of acute rejection. The following experiments examined transplant recipient serum and human heart, left ventricle, tissue for potential markers of heart transplant rejection. In these experiments, the efficacy of a modified serum solubilisation buffer was investigated and serum from transplant patients was used to detect anti-heart antibodies (i.e. anti-cardiac protein antibodies) generated by heart transplant recipients and to detect cardiac proteins in transplant recipient serum.

The presence of anti-heart antibodies was demonstrated by probing Western blots of 1-D SDS-PAGE separated human heart left ventricle proteins with transplant recipient serum. Rejection grade 3A serum (histologically confirmed) was used from two patients and the presence of IgM and IgG type antibodies was investigated. Bands from a non-blotted (CBBR stained) 1-DE gel of human heart left ventricle proteins that corresponded to immunoreactive bands of interest on Western blots were excised and subjected to mass spectrometry in order to identify potential antigens. Briefly, each protein band was enzymatically digested using trypsin. The collection of peptides so produced were separated by reversed phase chromatography using a 75 micron ID picofrit column and eluted directly into the electrospray ionisation (ESI) source fitted to a Q-Tof mass spectrometer. The Q-Tof was operated in a data dependant manner whereby the instrument was set to acquire MS/MS spectra for each eluting peptide present in survey scans. The complete MS/MS datasets for each band were submitted to the MASCOT algorithm (purchased from Matrix Science Ltd) for database searching to identify the protein(s) present. Several 1-DE bands were found to be immunoreactive (both IgM and IgG) on Western blots for both patients. Analysis of the corresponding bands on the gel by mass spectrometry provided the identity of several proteins present in each band. Notably, these experiments showed three proteins to be rejection-responsive as detailed in Table 2, namely a-Crystallin b chain (SWISS-PROT P02511), Tropomyosin α-chain (SWISS-PROT P09443), Myosin Light Chain 1 (SWISS-PROT P08590).

Development of Immunoassays

Mono- and/or polyclonal antibodies specific for the potential markers of acute rejection identified above from the proteomic analysis were employed in sensitive ELISA immunoassays to establish whether these proteins can be detected in the plasma of transplant patients. These proteins are then potential candidates for use as a non-invasive diagnostic and/or prognostic test for acute rejection following heart transplantation.

Monoclonal and polyclonal antibodies specific for tropomyosin, α-crystallin B chain and myosin light chain I were purified on protein G and protein A columns, and subsequently concentrated using Centricon filters. The purified antibodies were then used to establish competitive ELISA assays for the detection of these proteins in serum of heart transplant patients. The sensitivity of these assays was found to increase significantly by adapting the ELISA assay in combination with a chemiluminescent detection system. The assays currently have sensitivities approaching 1 ng/mL.

Figure 2:
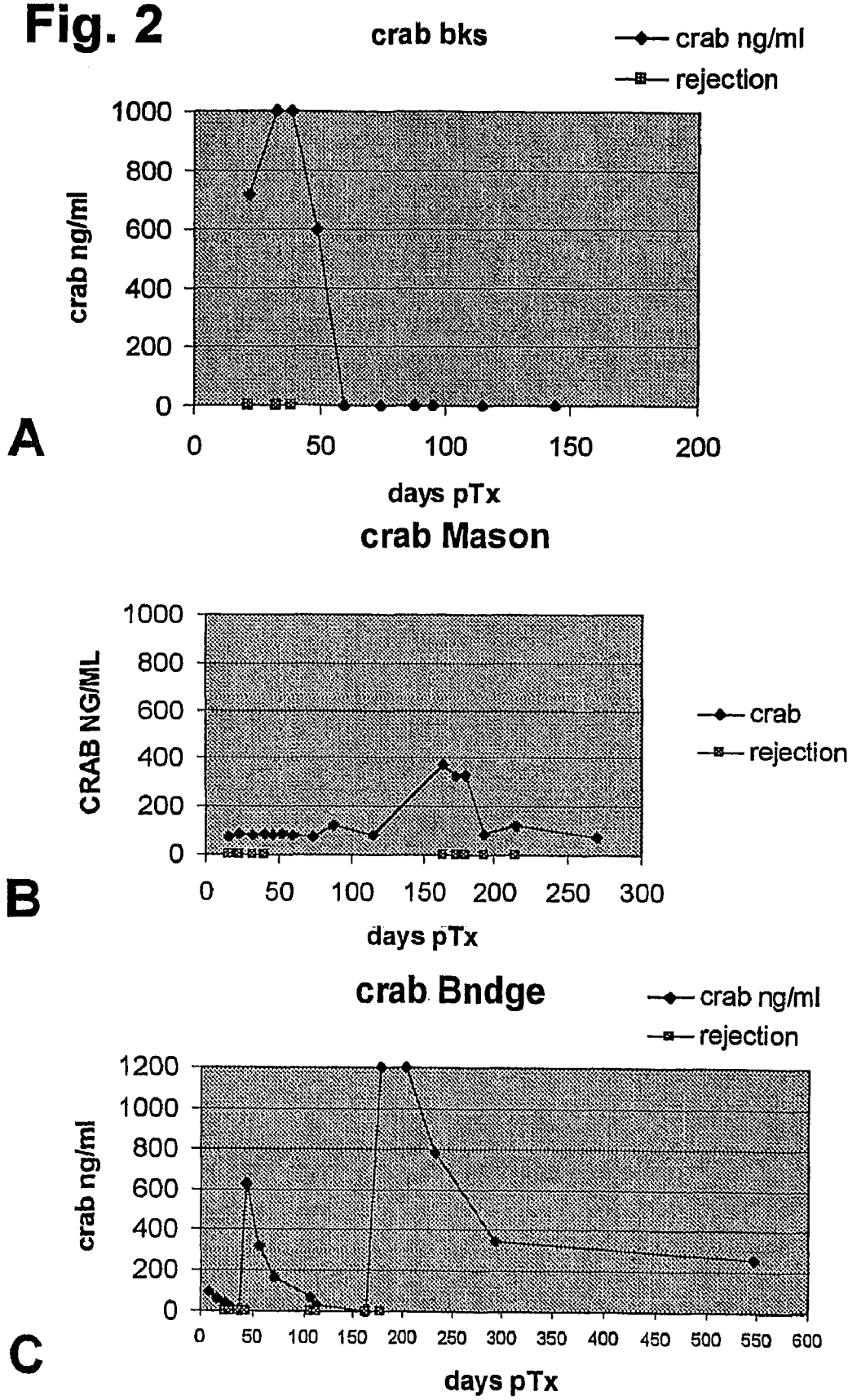
FIGS. 2A, B and C show the results of ELISA assays using α-crystallin B chain as a marker of acute rejection.

The ELISA assays were used to test sequential serum samples from REMAP patients to establish whether these antigens (tropomyosin, α-crystallin B chain and myosin light chain I) are useful non-invasive markers of acute rejection. Initial examples of the results are shown in FIGS. 2 and 3 for the α-crystallin B chain and tropomyosin assays respectively. In both cases, the proteins of interest can be detected in the serum of the patients early after transplantation. Serum levels of the proteins are elevated at certain times and there is some indication that these increased levels are associated with episodes of acute rejection.

In conclusion, the ELISA assays that we have developed are able to detect antigens of interest in the serum of patients following cardiac transplantation and the initial data suggest that there may be an association between increased serum levels of these proteins with the occurrence of episodes of acute rejection.

TABLE 1

Computer Analysis Data: IPG 3-10 NL VS 12% SDS-PAGE

This table shows the numbers of proteins that are significantly changed in abundance (increased or decreased) at different fold-change threshold values (2- to 5-fold) in biopsies taken at the time of acute rejection (R) compared with biopsies taken when no rejection was occurring (NR).

| Patient | Biopsies (NR/R) | 2-fold increase | 2-fold decrease | 3-fold increase | 3-fold decrease | 4-fold increase | 4-fold decrease | 5-fold increase | 5-fold decrease |
|---|---|---|---|---|---|---|---|---|---|
| BB | 7(3/4) | 143 | 183 | 69 | 98 | 39 | 56 | 19 | 35 |
| BK | 6(2/4) | 112 | 104 | 87 | 34 | 42 | 15 | 24 | 12 |
| HD | 10(7/3) | 84 | 184 | 35 | 85 | 15 | 46 | 10 | 26 |
| LY | 10(5/5) | 180 | 222 | 94 | 113 | 61 | 75 | 47 | 52 |

TABLE 2

Identities of Potential Markers of Acute Rejection
(see FIG. 1)

| SPOT # | PROTEIN NAME | SWISS-POT ACCESSION NUMBER | SWISS-POT IDENTITY | EXPRESSION DURING MILD ACUTE REJECTION |
|---|---|---|---|---|
| 1 | Myosin regulatoiy light chain 2, ventricular/cardiac isoform (MLC2) | P10916 | MLRV_HUMAN | 3 fold increase 3 fold decrease |
| 2 | Tropomyosin α-chain (TPM1) (fragment) | P09493 | TPM1_HUMAN | 3 fold increase 3 fold decrease |
| 3 | Troponin C, slow skeletal and cardiac muscle | P02590 | TPCC_HUMAN | 3 fold increase 3 fold decrease |
| 4 | Actin, α-cardiac (fragment) | P04270 | ACTC_HUMAN | 3 fold increase |
| 5 | Actin, α-cardiac (fragment) | P04270 | ACTC_HUMAN | 3 fold increase |
| 6 | Heat shock protein 27kDa (HSP27) | P04792 | HS27_HUMAN | 3 fold increase |
| 7 | Myoglobin | P02144 | MYG_HUMAN | 3 fold decrease |
| 8 | Peroxisomal enoyl-CoA hydratase | Q13011 | ECH1_HUMAN | 3 fold decrease |
| 9 | Not identified | — | — | 3 fold decrease |
| 10 | Not identified | — | — | 3 fold decrease |
| 11 | Tropomyosin α-chain (TPM1) | P09443 | TMP1_HUMAN | 3 fold increase |
| 12 | α-Crystallin B chain | P02511 | CRAB_HUMAN | 3 fold increase |
| 13 | Myosin light chain 1, ventricular isoform MLC1) | P08590 | MLEV_HUMAN | 3 fold decrease |

REFERENCES

The references cited herein are all expressly incorporated by reference.

[1] Billingham M E, Cary N R B, Hammond M E, Kemnitz J, Marboe C, McCallister H A, Snovar D C, Winters G L and Zerbe A. A working formulation for the standardisation of nomenclature in the diagnosis of heart and lung rejection: heart rejection study group. J Heart & Lung Transplant. 1990, 9: 587–593.

[2] Yousem S A, Berry G J, Brunt E M, Chamberlain D, Hruban R H, Sibley R K, Stewart S, Tazelaar H. A working formulation for the standardisation of nomenclature in the diagnosis of heart and lung rejection: lung rejection study group. J. Heart & Lung Transplant., 1990, 9: 593–598.

[3] Smart F W, Young J B, Weilbaecher D, Kleiman N S, Wendt R E, Johnston D L. Magnetic resonance imaging for assessment of tissue rejection after heterotopic heart transplantation. H.Heart Lung Transplant. 1993, 12: 403–10.

[4] Lacroix D, Kacet S, Savard P, et al. Signal averaged electrocardiography and detection of heart transplant rejection: comparison of time and frequency domain analysis. J. Am. Coll. Cardiol. 1992, 19: 553–8.

[5] Dodd D A, Brady L D, Carden K A, Frist W H, Boucek M M, Boucek R J. Pattern of Echocardiographic abnormalities with acute cardiac allograft rejection in adults: correlation with endomyocardial biopsy. J. Heart & Lung Transplant. 1993, 12:1009–17.

[6] Koelman C A, Vaessen L M, Balk A H, Weimar W, Doxiadis I I, Class F H. Donor derived soluble HLA plasma levels can not be used to monitor graft rejection in heart transplant recipients. Transplant. Immunol., 2000, 8: 57–64.

[7] Suitters A J, Rose M L, Dominguez M J, Yacoub M H. Selection for donor-specific cytotoxic T lymphocytes within the allografted human heart. Transplantation 1990, 49: 1105–1109.

[8] Jutte N H, Knoop C J, Heijse P, Balk A H, Mochtar B, Claas F H, Weimar W. H. Human heart endothelial-restricted allorecognition. Transplantation 1996, 62: 403–406.

[9] Weis M, Wildhirt S M, Schulz C, Pehlivanli S, Fraunberger P, Meiser B M, von Scheidt W. Modulation of coronary vasomotor tone by cytokines in cardiac transplant recipients. Transplantation 1999, 68: 1263–7.

[10] Smith J D, Danskine A J, Rose M L, Yacoub M H. Specificity of lymphocytotoxic antibodies formed after cardiac transplantation and correlation with rejection episodes. Transplantation 1992, 53: 1358–1362.

[11] Trull A, Steel L, Cornelissen J, Smith T, Sharples L, Cary N, Stewart S, Large S, Wallwork J. Association between blood eosinophil counts and acute cardiac and pulmonary allograft rejection. J. Heart & Lung Transplantation 1998, 17: 517–24.

[12] Katus H A, Looser S, Hallermayer K et al. Development and in vitro characterisation of a new immunoassay of cardiac troponin T. Clin. Chem. 1992, 38: 386–93.

[13] Katus H A, Remppis A, Neumann F J et al. Diagnostic efficiency of troponin T measurements in acute myocardial infarction. Circulation 1991, 83: 902–12.

[14] Katus H A, Schoeppenthau M, Tanzeem A, et al. non-invasive assessment of perioperative myocardial cell damage bu circulating cardiac troponin T. Brit. Heart J. 1991, 65: 259–64.

[15] Zimmerman R, Baki S, Dengler T J et al. Troponin T release after heart transplantation. Brit. Heart J., 1993, 69: 395–8.

[16] Dengler T J, Zimmerman R, Braun K, Muller-Bardoff M, Zehelein J, Falk-Udo Sack, Schnabel P A, Kubler W, Katus H. Elevated serum concentrations of cardiac troponin T in acute allograft rejection after human heart transplantation. J. Am Coll Cardiol., 1998. 32: 405–12.

[17] Faulk W P, Labarrere C A, Torry R J, Nelson D R. Serum cardiac troponin-T concentrations predict development of coronary artery disease in heart transplant recipients. Transplantation, 1998, 66: 1335–9.

[18] Vijay P, Scavo V A, Morelock R J, Sharp T G, Brown J W. Donor cardiac troponin-T: a marker to predict heart transplant rejection. Ann Thorac. Surg., 1998, 66: 1034–9.

The invention claimed is:

1. A method for diagnosis or prognosis of acute rejection of a transplanted organ, the method comprising determining an amount of nonfragmented tropomyosin 1 α-chain protein, in a sample from a patient who has received said transplanted organ, wherein an increase in the amount of the tropomyosin 1 α-chain said sample compared to a normal control is indicative of said acute rejection.

2. The method of claim 1, wherein the method comprises the steps of:
   (a) contacting said sample from a patient with a solid support having immobilized thereon a binding agent having binding sites which are effective to specifically bind to said protein under conditions in which said protein binds to the binding agent; and,
   (b) determining the amount of said protein bound to the binding agent.

3. The method of claim 2, wherein step (b) comprises (i) contacting the solid support with a developing agent which is effective to bind to occupied binding sites, or unoccupied binding sites or said protein, the developing agent comprising a label and (ii) detecting the label to obtain a value representative of the amount of said protein in the sample.

4. The method of claim 3, wherein the label is a radioactive label, a fluorophor, a phosphor, a laser dye, a chromogenic dye, a macromolecular colloidal particle, a latex bead which is coloured, magnetic or paramagnetic, an enzyme which catalyses a reaction producing a detectable result or the label is a tag.

5. The method of claim 2, wherein in step (b) said protein is labelled to allow detection of said protein when bound to the binding agent.

6. The method of claim 2, wherein the binding agent immobilized on the solid support is an antibody which is effective to bind to the Tropomyosin 1 α-chain protein.

7. The method of claim 2, wherein the method employs a plurality of binding agents immobilized as predefined locations on the solid support.

8. The method according to claim 1, wherein the transplanted organ is a heart, a kidney, a liver, a lung, a pancreas or a small bowel transplant.

9. The method according to claim 1, wherein the acute rejection is in a period of 6 months following said organ transplant.

10. The method according to claim 1, wherein the method comprises determining an amount of at least one further protein marker, wherein said at least one further protein marker is selected from the group consisting of:
   an increase in the amount of troponin C;
   an increase in the amount of actin α-cardiac protein;
   an increase in the amuont of heat shock protein 27 kDa;
   a decrease in the amount of peroxisomal enoyl-CoA hydratase;
   an increase in the amount of α-crystallin B chain.

11. The method according to claim 1, wherein said sample is selected from a blood sample and a serum sample.

* * * * *